(12) United States Patent
Hamilton

(10) Patent No.: US 6,660,519 B2
(45) Date of Patent: Dec. 9, 2003

(54) HIGH THROUGHPUT METHOD, APPARATUS AND KIT FOR PLATING MICROORGANISMS AND CELL CULTURES

(75) Inventor: Carol Hamilton, Apex, NC (US)

(73) Assignee: Paradigm Genetics, Inc., Research Triangle Park, NC (US)

(*) Notice: Subject to any disclaimer, the term of this patent is extended or adjusted under 35 U.S.C. 154(b) by 13 days.

(21) Appl. No.: 10/076,712

(22) Filed: Feb. 15, 2002

(65) Prior Publication Data

US 2003/0157706 A1 Aug. 21, 2003

(51) Int. Cl.[7] ................................................. C12M 1/26
(52) U.S. Cl. ..................................................... 435/309.1
(58) Field of Search ............................ 435/309.1, 309.4

(56) References Cited

U.S. PATENT DOCUMENTS

| 4,053,362 A | * | 10/1977 | Sforza | ........................ 435/243 |
| 5,869,321 A | * | 2/1999 | Franklin | .................. 435/253.6 |
| 5,952,191 A | * | 9/1999 | Morozov | ...................... 435/30 |

* cited by examiner

*Primary Examiner*—David A. Redding
(74) *Attorney, Agent, or Firm*—Deborah H. Spencer; Timothy G. Hofmeyer; Laura L. Kiefer

(57) ABSTRACT

The present invention relates to a highly effective method, apparatus and kit for growing and plating out cultures of microorganisms or cell culture, especially derived from culture blocks containing multiple wells, such as a 96-well or 384-well plate or block.

54 Claims, 7 Drawing Sheets

HIGH THROUGHPUT METHOD, APPARATUS AND KIT FOR PLATING MICROORGANISMS AND CELL CULTURES

FIELD OF THE INVENTION

The present invention relates to a highly effective method, apparatus and kit for growing microorganisms or cell cultures from organisms such as plants or animals, especially derived from culture blocks containing multiple wells, such as a 96-well or 384-well plate or block.

BACKGROUND OF THE INVENTION

Experiments involving biotechnology include the use of biological systems such as genetically engineered microorganisms or cell cultures. In order to prepare such microorganisms or cell cultures, new genetic material usually in the form of DNA (deoxyribonucleic acid) fragments, is inserted into the microorganisms or cell culture. If successfully inserted, the genetic makeup of the treated microorganisms or cell culture will be changed so that it can express a new trait (e.g. making a new protein). In a traditional method, a sample of a treated microorganisms or cell culture is grown by spreading an aliquot of liquid culture containing the microorganisms or cell culture onto the surface of an individual petri plate containing agar-based medium. Turntables and hand-held spreaders to facilitate this process are commercially available (VWR). In this traditional method, however, only one sample at a time can be handled, requiring considerable time, labor and expense to grow the microorganisms or cell cultures on individual plates. Thus, a new approach was sought to develop a high-throughput system and method that would enable one to grow multiple samples of microorganisms or cell cultures, especially from plates or blocks containing multiple wells of microorganisms or cell cultures.

SUMMARY OF THE INVENTION

In one embodiment, the present invention is directed towards a method for plating microorganisms or cell cultures, comprising:
  a) using an apparatus comprising
    i) a tray having a bottom and sidewalls extending from said bottom;
    ii) a plurality of substantially uninterrupted parallel dividers, each divider having a length and a height;
    iii) means for maintaining said dividers substantially parallel within said tray, wherein said dividers are removable from said tray;
    iv) agar that fills said tray to a point less than the height of said dividers in said tray, wherein said agar has a surface for plating microorganisms or cell cultures that is defined as a lane between two adjacent dividers or a lane between a divider and an adjacent sidewall; and
    v) beads that can fit between said substantially parallel dividers;
  b) contacting said beads with a source of microorganisms or cell culture; and
  c) rolling said beads with said microorganisms or cell culture along said agar surface to plate said microorganisms or cell culture.

In another embodiment, the present invention is directed towards an apparatus comprising:
  a) a tray having a bottom and sidewalls extending from said bottom;
  b) a plurality of substantially uninterrupted parallel dividers, each divider having a length and a height; and
  c) means for maintaining said dividers substantially parallel within said tray, wherein said dividers are removable from said tray.

In another embodiment, the present invention is directed towards an apparatus comprising:
  a) a tray having a bottom and sidewalls extending from said bottom;
  b) a plurality of substantially uninterrupted parallel dividers, each divider having a length and a height;
  c) means for maintaining said dividers substantially parallel within said tray, wherein said dividers are removable from said tray; and
  d) a cover for covering said tray and said dividers.

In another embodiment, the present invention is directed towards an apparatus comprising:
  a) a tray having a bottom and sidewalls extending from said bottom;
  b) a plurality of substantially uninterrupted parallel dividers, each divider having a length and a height;
  c) means for maintaining said dividers substantially parallel within said tray, wherein said dividers are removable from said tray;
  d) a cover for covering said tray and said dividers; and
  e) beads that can fit between said substantially parallel dividers.

In another embodiment, the present invention is directed towards an apparatus comprising:
  a) a tray having a bottom and side walls extending from said bottom;
  b) a plurality of substantially uninterrupted parallel dividers, each divider having a length and a height;
  c) means for maintaining said dividers substantially parallel within said tray, wherein said dividers are removable from said tray;
  d) a cover for covering said tray and said dividers; and
  h) agar that fills said tray to a point less than the height of said dividers in said tray, wherein said agar has a surface for plating microorganisms or cell culture that is defined as a lane between two adjacent dividers or a lane between a divider and an adjacent sidewall.

In another embodiment, the present invention is directed towards an apparatus comprising:
  a) a tray having a bottom and sidewalls extending from said bottom;
  b) a plurality of substantially uninterrupted parallel dividers, each divider having a length and a height;
  c) means for maintaining said dividers substantially parallel within said tray, wherein said dividers are removable from said tray;
  d) a cover for covering said tray and said dividers; and
  h) agar that fills said tray to a point less than the height of said dividers in said tray, wherein said agar has a surface for plating microorganisms or cell culture that is defined as a lane between two adjacent dividers or a lane between a divider and an adjacent sidewall.

In another embodiment, the present invention is directed towards a kit comprising in a single package:
  a) a tray having a bottom and sidewalls extending from said bottom;
  b) a plurality of substantially uninterrupted parallel dividers, each divider having a length and a height; and c) means for maintaining said dividers substantially parallel within said tray, wherein said dividers are removable from said tray.

The method, apparatus or kit of the present invention can utilize or have a plurality of dividers, preferably at least eleven or more dividers. The tray, the dividers, the means for maintaining the dividers parallel (such as supporting ribs), can be plastic. The tray and the dividers can be selected from a plastic, which is polycarbonate, polystyrene, polypropylene or combinations thereof.

The method, apparatus or kit of the present invention can have a means for maintaining the dividers substantially parallel. The means for maintaining the dividers substantially parallel can be at least one supporting rib. The maintaining means can also be at least two, three, four, five or more supporting ribs.

The method, apparatus or kit of the present invention can include a tray, which has an interior length and an interior width and the divider length can be less than the length of the interior of the tray. The divider length can preferably be from about 75% to about 95% of the interior length of the tray. The method, apparatus or kit of the present invention can also include a cover and the cover can be removable from the tray.

The method, apparatus or kit of the present invention can also include beads. Preferably, the beads can be spherical (ball or ball-shaped) or even cylindrical. Also preferred is that the bead are made of glass. In addition, the method, apparatus or kit can also have a starting gate. The dividers used in the present invention can have at least one notch along the edge of the divider length and the starting gate can rest upon the notch in each of the dividers.

The method, apparatus or kit can further have an exit-gate whose removal defines an exit-alley within the tray. The exit-alley can thereby communicate with at least one sidewall of the tray, which can have at least one aperture therein. The method, apparatus or kit can also comprise a tray and dividers that are substantially sterile.

The present invention has the advantage of providing a method, apparatus or kit for plating microorganisms or cell culture that requires significantly less time and fewer personnel to perform compared with other known methods.

Another advantage of the present invention is that it provides a method, apparatus or kit for plating microorganisms or cell culture in a high-throughput manner that can utilize different types of microorganisms or cell cultures on the same plate.

DETAILED DESCRIPTION OF INVENTION

The term "agar" refers to a polysaccharide extract of certain seaweed used as an inert support or solidifying agent for the growth of cells, particularly bacteria, plant cells or animal cells.

The term "cell culture" refers to cells derived from plants or animals and maintained in a suitable growth media. Such cells are typically clonal, i.e. clones derived from plant or animal cells or tissues.

The terms "colony" refers to a contiguous source of single cells, such as bacteria, plant cells or animal cells, derived from a single ancestor and growing on a solid surface or inert support, such as agar. The term "colonies" is the plural of "colony."

The terms "microoganisms" or "microorganism cultures" can be considered substantially synonymous, and refer to living organisms too small to be perceived with the unaided or naked eye, esp. bacterium, fungus, protozoa or intracellular parasites. The term "microorganism" is the singular form of "microorganisms."

The term "sterile" refers to an apparatus being substantially free of microorganisms. It will be understood by one of ordinary skill in the art that the term "sterile" can also encompass the presence of some microorganisms that grow slowly and would not interfere with the practicing of the method of the present invention. Typically, the present invention can be made sterile by such methods as autoclaving, radiation, and chemical treatments, effectively killing most of the microorganisms before use thereof.

Figure 1:
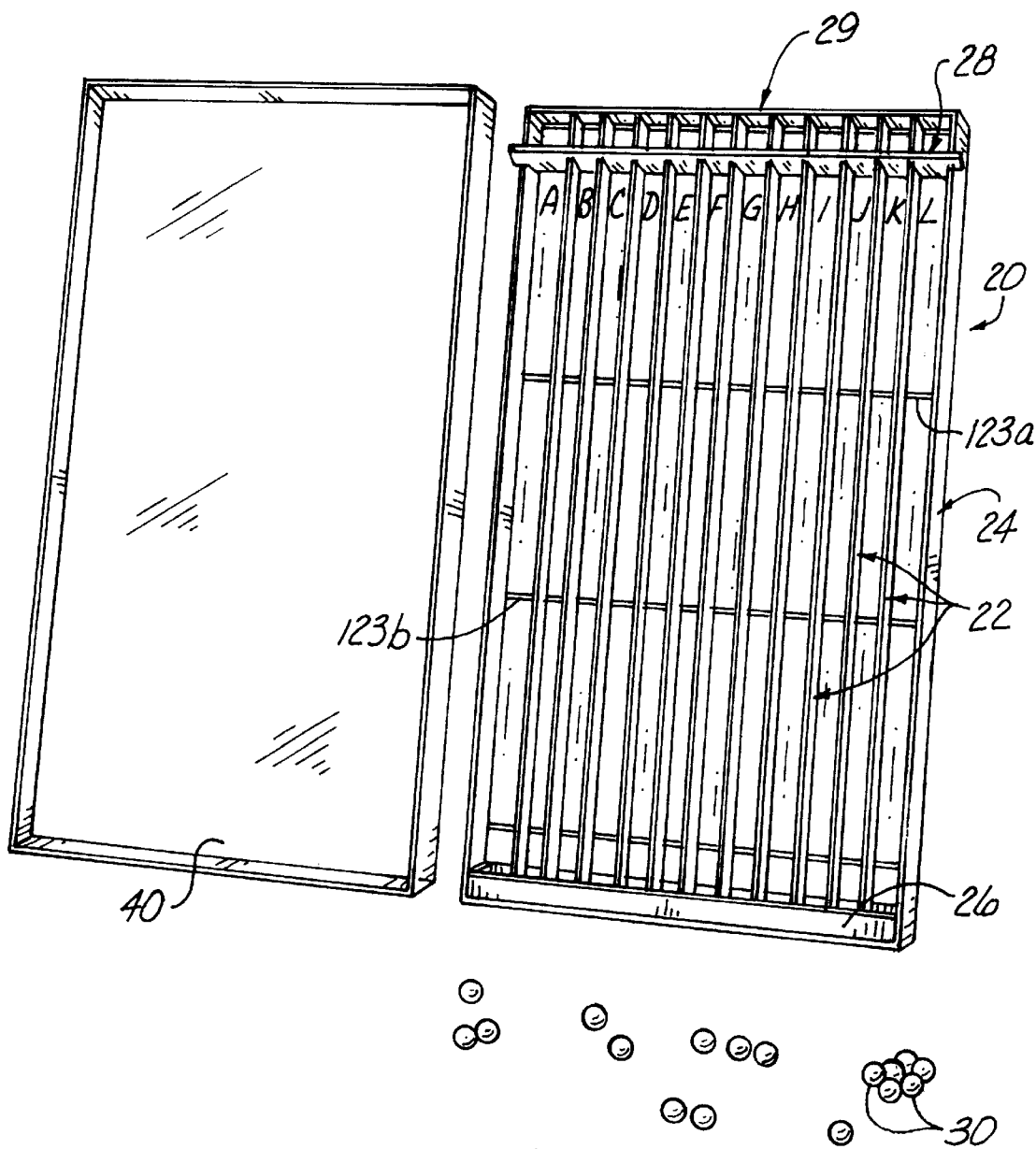
FIG. 1 shows a vertically positioned, assembled multi-channel plating unit 20 of the present invention prior to addition of agar.

In FIG. 1 shows assembled multi-channel plating unit 20 made up of removable dividers 22, tray 29, removable start-gate 28, removable exit gate or block 26, beads 30 and covering lid 40. Lanes are defined as the space between two adjacent dividers, such as lanes "J" and "K." Unit 20 is shown vertically primarily for the purpose of display. When unit 20 is placed in a horizontal position, the unit is ready to receive addition of liquid agar. In a preferred embodiment, the total width of the unit (~10.8 cm) and channel width (~0.9 cm) corresponds to a standard 96 well culture dish. The length of the prototype unit can range from about 18 cm to about 30 cm, although the length can be made longer or shorter depending upon the particular application. In this embodiment, there are eleven dividers 22, creating twelve lanes A, B, C, D, E, F, G, H, i, J, K and L, that run the length of unit 20 up to exit alley 27. In a preferred embodiment, the dividers do not run the complete interior length of the tray. Instead, the dividers may run anywhere from about 75% to about 95% of the interior length of the tray. In an alternate embodiment, however, the tray may be notched on opposing sides, such as the start gate side and the exit alley side. In this alternative embodiment, the dividers may run the entire length of the tray or even longer and may be supported by the notches in the tray sides. In this alternative embodiment, the tray sides may provide support for the dividers and can provide a means for maintaining the dividers substantially parallel. The lane dividers 22 create a barrier at and above the surface of the agar (not present), and can be raised off of the top of tray 29 to facilitate pouring the agar. In this embodiment, dividers 22 are a one-piece assemblage that are held together and substantially parallel by a maintaining means such as supporting ribs 123a and 123b. The present invention may use any number of means for supporting ribs that one may need to hold the dividers substantially parallel. Preferably, there are at least three supporting ribs that hold the dividers together and maintain them substantially parallel. One of ordinary skill in the art will recognize other means that can be used support and maintain the dividers substantially parallel. For example, a solid or continuous flooring can be used to connect the bottom of the dividers maintaining them substantially parallel within the tray. Alternatively, posts can be attached to the bottom of the tray. Another means of maintaining the dividers substantially parallel is to insert posts cross-sectionally through the dividers.

By use of the terminology "substantially parallel," it is meant that the dividers can still be parallel even though variably spaced to some extent as long as the beads are able to roll down the surface of the agar without obstruction. Preferably, parallel dividers 22 are not interrupted by inserts or extensions that may interfere with the beads rolling down the agar surface. For example, by use of the terminology "not interrupted," it is meant that the dividers define open lanes and that there are no cross-sectional divisions substantially blocking those lanes. There is a loose-fitting covering lid 40 that fits over unit 24 without agar so that the unit, optionally, can be covered and inverted during incubation of the microorganisms or cell culture. The covering lid may be any means, which keeps the apparatus free from contaminants throughout its operation of growing the desired microorganisms or cell culture. For example, the covering lid may be any means by which the interior of the tray and dividers are substantially closed off from the outside environment. Covering lid 40 can also be a plastic bag or wrap such as aluminum foil, to envelop the entire apparatus. A start-gate 28 is put in place after the agar media has been poured and has solidified. Start-gate 28 sits (temporarily) on the surface of the solidified agar and holds glass bead 30 or glass beads 30 in place. There is an exit-gate 26 that occupies an exit alley 27 and aperture 25 (both not shown). Exit-gate 26 is secured at the end of unit 24 before the liquid or viscous agar media is poured, then removed after the media has solidified.

Figure 2:
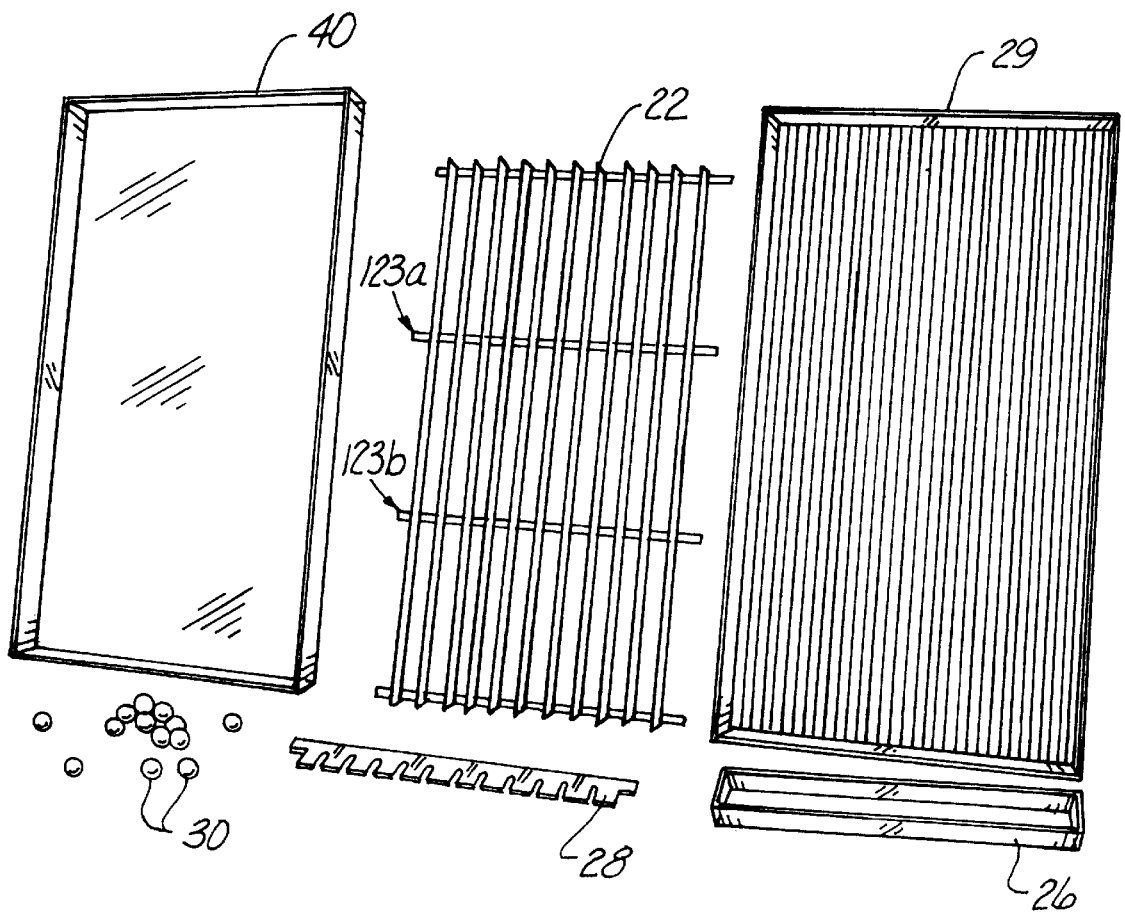
FIG. 2 shows the components that make up the multi-channel plating unit 20.

FIG. 2 shows the components that make up the multi-channel plating unit 20, including tray 29, dividers 22 supported by supporting ribs 123a and 123b, removable start gate 28, removable exit gate 26, balls or beads 30 and covering lid 40.

Figure 3:
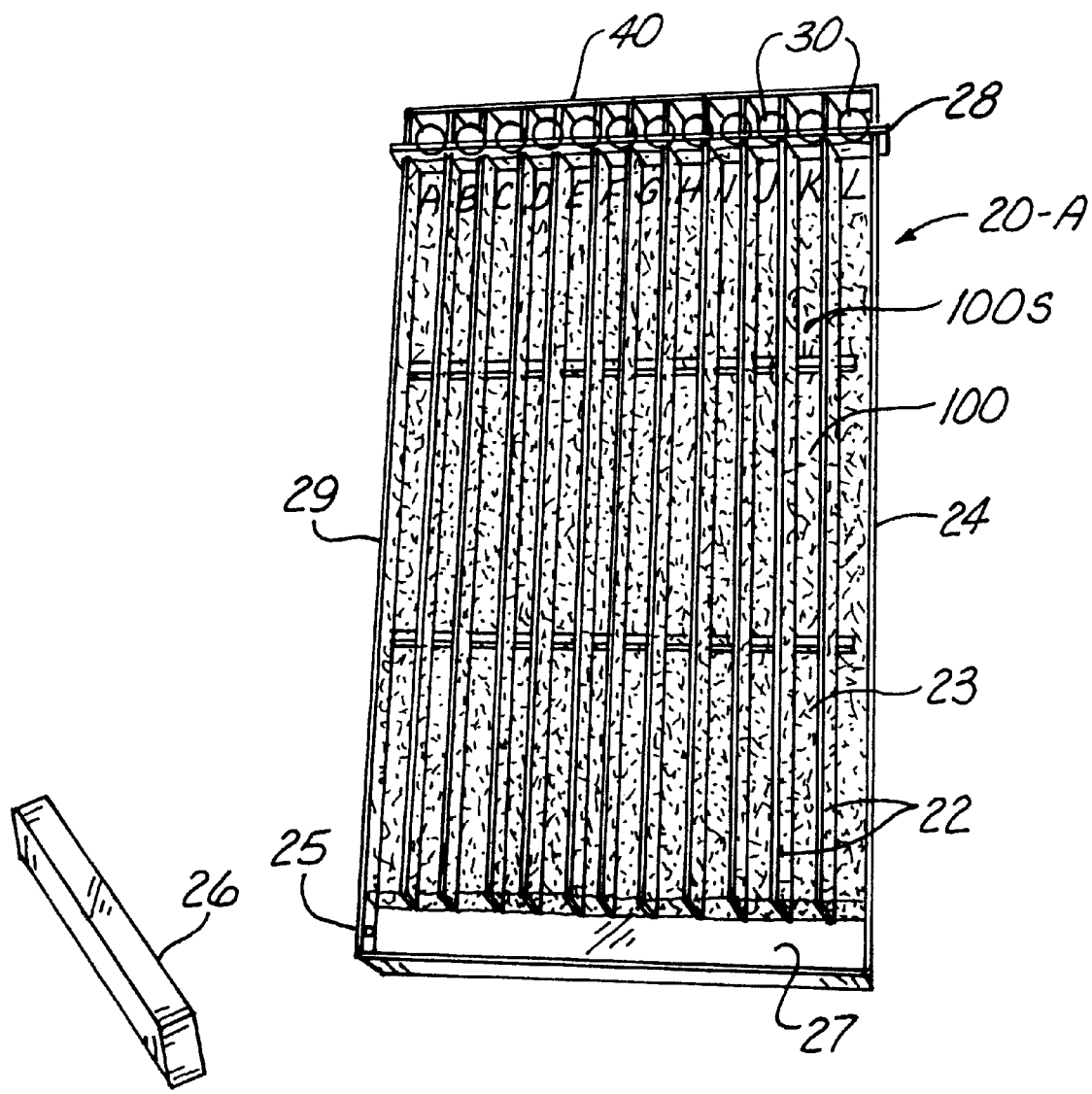
FIG. 3 shows the shows a multi-channel plating unit 20-A after addition of agar with the removal of exit gate from the unit.

FIG. 3 shows the shows a multi-channel plating unit 20-A ("A" designates the unit contains agar) after solidification of agar 100 and removal of exit-gate or block 26. Multi-channel plating unit 20-A is made of dividers 22, tray 29, removable start-gate 28, beads 30 and agar 100 having a surface 100s in lanes A–L. Exit-gate 26 has been removed from unit 20-A to provide exit alley 27 leading to aperture or hole 25 in tray 29. There are no dividers in exit alley 27. However, one of ordinary skill in the art could extend the dividers the entire interior length of the tray and forego the optional exit alley 27. In one embodiment, there is a hole or aperture 25 in one corner of exit alley or trap 27 large enough to allow the beads to exit the unit 20-A for subsequent reuse or disposal. Alternatively, multiple apertures can be used to exit the beads from the unit. Unit 20-A makes use of sterile glass beads 30 to spread the bacterial culture down alleys A–L. The beads 30 are shaped and sized so that they are capable of rolling down the lanes created by the substantially parallel dividers. Generally, a spherical or cylindrical shape is preferred. While the present invention covers other shapes, the beads should be capable of rolling down the lanes. The beads are preferably made from glass, but can be made from metal or a plastic. Preferably the beads can be sterilized prior to use. Also preferred is that the beads can be recycled and re-sterilized prior to use.

After adding an aliquot of liquid culture containing microorganisms or cell culture to balls or beads 30, unit 20-A is gently agitated so that beads 30 are rocked between the top edge 40 of 20-A and start gate 28 to promote even coating of the beads. Unit 20-A is slightly tilted or balanced so that when start gate 28 is removed, beads 30 can roll down the surface 100s of the agar 100 into exit alley 27 and exit unit 20-A through aperture 25.

Figure 4:
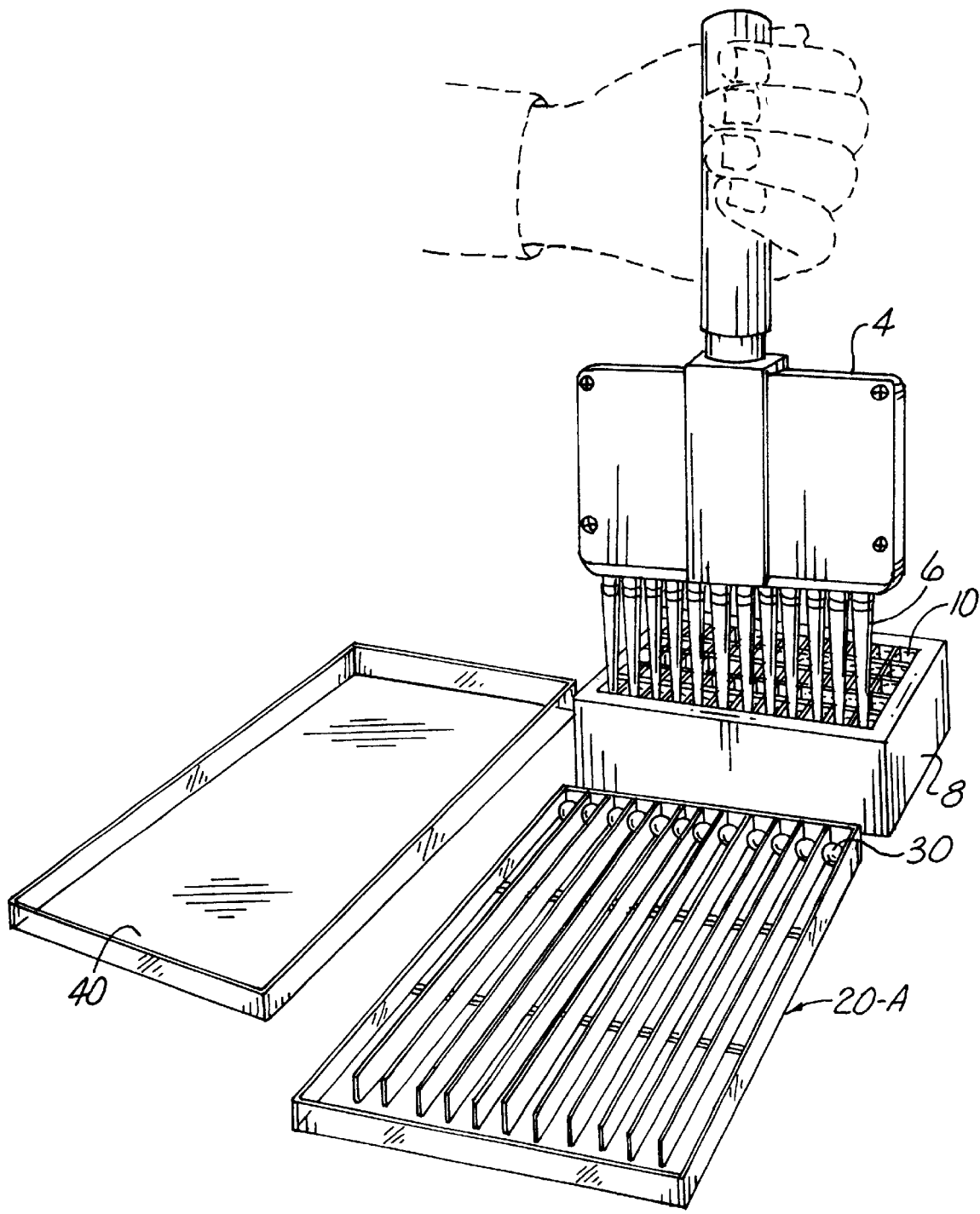
FIG. 4 shows the withdrawal of multiple liquid aliquots containing microorganisms or cell culture from a 96-well block using a multi-channel pipette.

FIG. 4 shows the withdrawal of multiple liquid aliquots (not shown) containing microorganisms or cell culture from an 12×8 96-well block 8 having 96 wells, cells or vertical channels 10 using multi-channel pipette 4 that utilizes disposable pipette tips 6 to withdraw and deposit the liquid aliquots. The microorganisms or cell culture selected from the 96-well block can be from the same source or different sources, thus allowing differing microbial strains to be plated or grown on the multi-channel plating unit 20-A. In this figure, multi-channel pipette 4 is shown with 12 pipette tips (corresponding to lanes A–L), although greater or fewer pipette tips can be employed, depending on the construction of the multi-channel pipette. Multi-channel pipette will be applying the multiple aliquots to multi-channel plating unit 20-A containing agar and beads 30.

Figure 5:
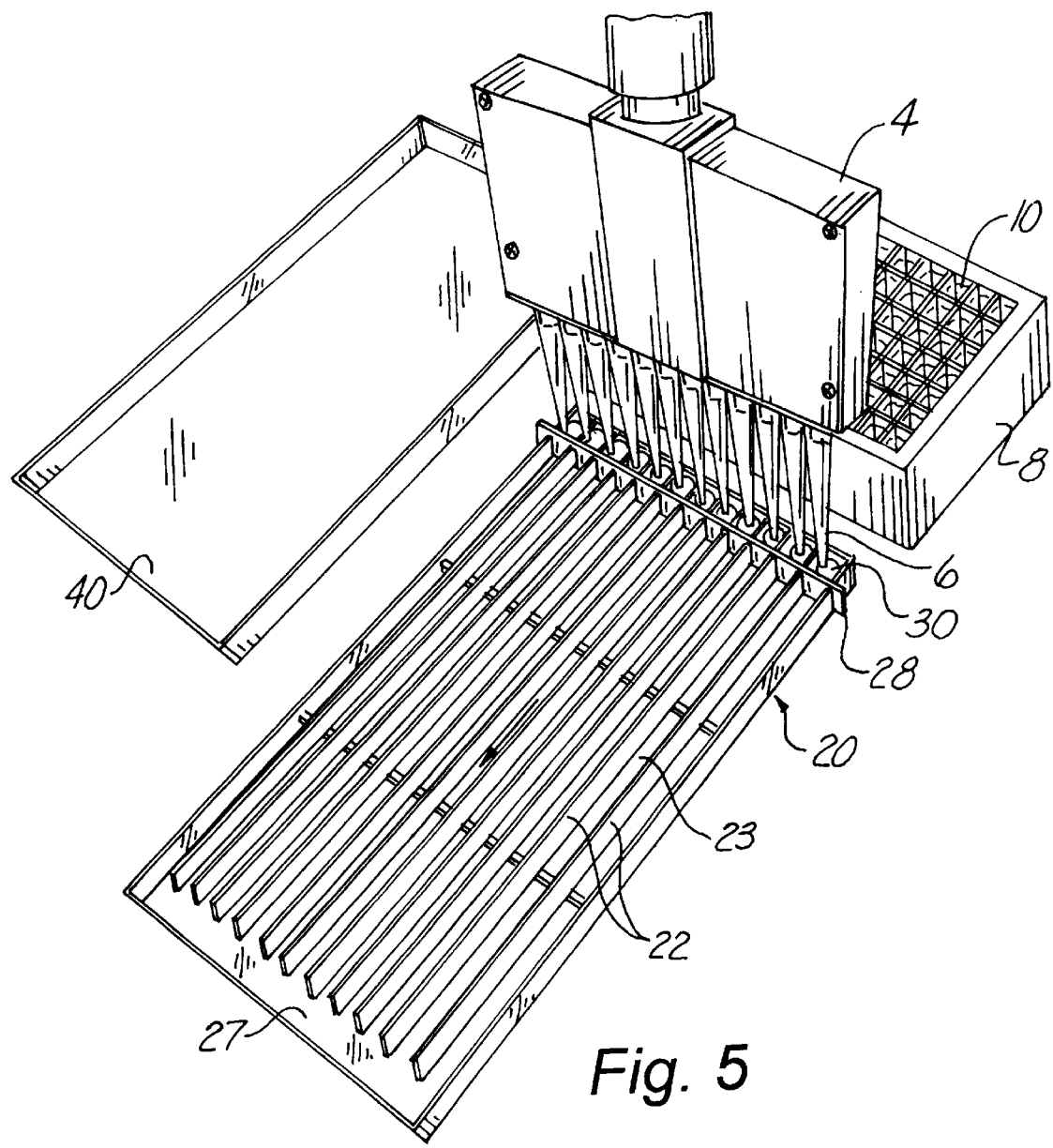
FIG. 5 shows the addition of the multiple liquid aliquots containing microorganisms or cell culture to beads within multi-channel plating unit 20.

FIG. 5 shows the addition of the multiple liquid aliquots containing microorganisms or cell culture to beads 30 within multi-channel plating unit 20-A. After the liquid aliquots containing the microorganisms or cell culture have been withdrawn from individual wells 10 in multi-well block 8 by pipette tips 6, the aliquots are deposited or pipetted onto beads 30 located between the end of tray 20 and start gate 28. The arrow in the center of plating unit 20-A shows the direction for beads 30 to travel.

Figure 6:
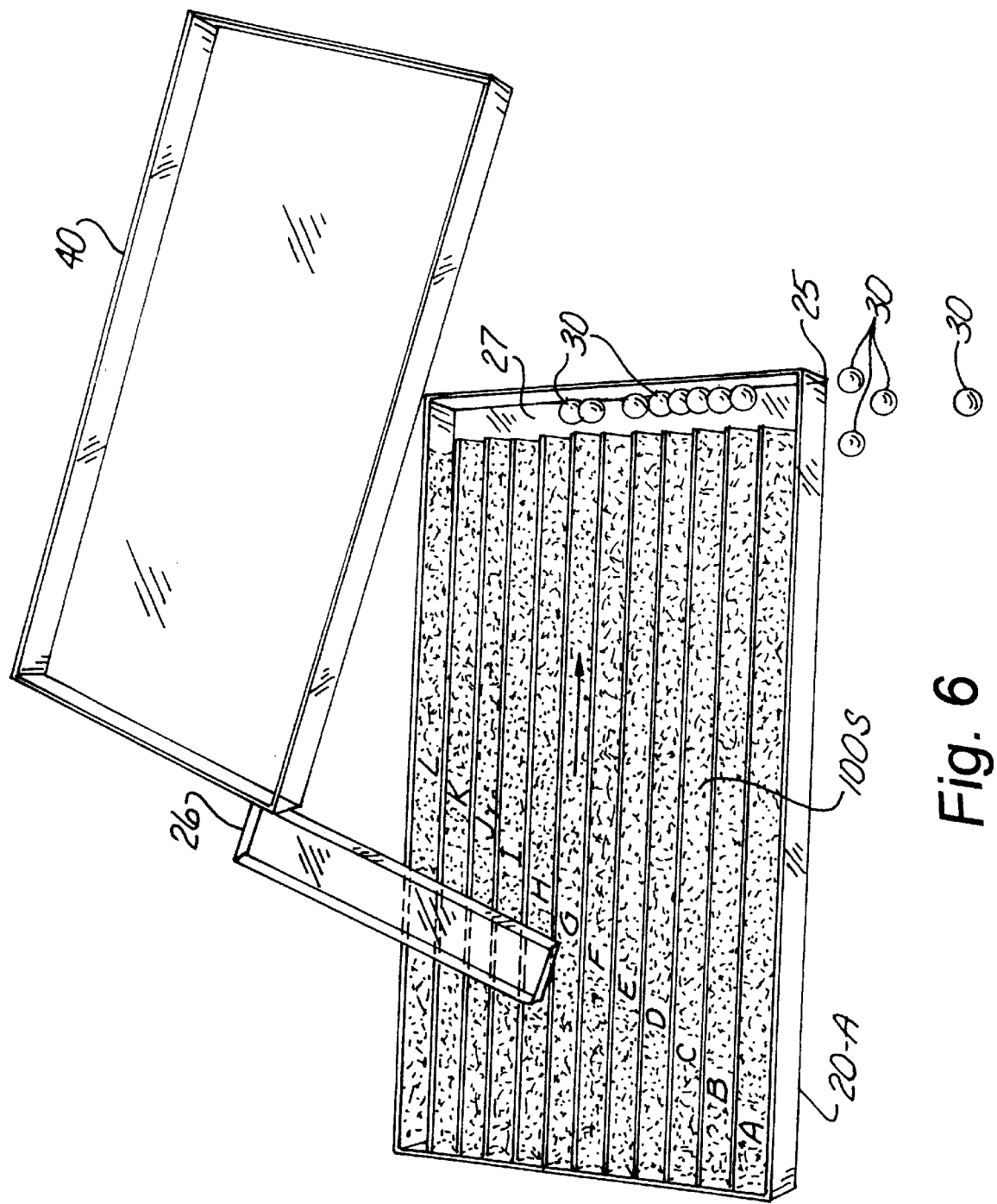
FIG. 6 shows the direction of movement of beads down multi-channel plating unit 20 and their exit from the unit.

FIG. 6 shows the direction of movement of beads 30 down lanes A–L of multi-channel plating unit 20-A and their deposit into exit-trap 27 and from unit 20-A through aperture 25. As glass beads 30 that have received the liquid deposits of microorganisms or cell culture roll across agar surface 100s, the beads thinly spread or coat the bacterial culture onto and/or along surface 100s in only a single roll of the bead(s) down alleys A–L. Alternatively, beads 30 can be rolled back and forth within the lanes before their exit or removal from the unit. In the present embodiment, the beads can be rolled back and forth after reinserting the end block or using any other means to block the exit alley. After coating the lanes with the microorganisms or cell culture, beads 30 are removed from unit 20-A, lid 40 is placed over or on top of the agar-facing side of unit 20-A, and the combined unit 20-A with the attached lid is turned over to allow the microorganisms or cell culture to incubate or grow in lanes A–L. Unit 20-A is turned over with lid 40 facing downward to minimize any water condensing on lid 40 from entering and possibly contaminating lanes A–L.

Figure 7:
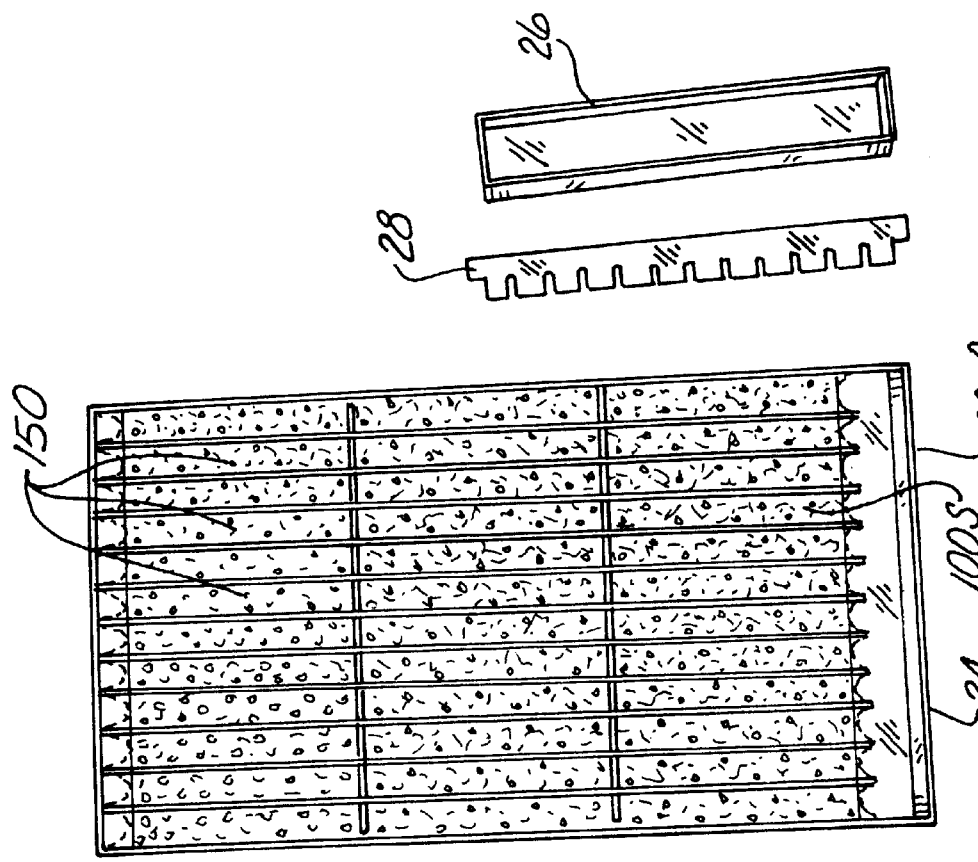
FIG. 7 shows the growth of individual microorganisms colonies on the agar surface after incubation of the plates.
Figure 7:
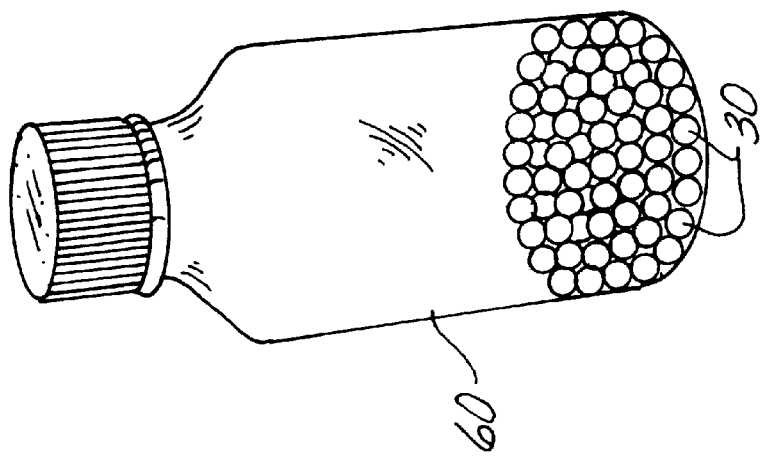

FIG. 7 shows the growth of individual dot-like microorganism colonies 150 growing on and/or along agar surface 100s after incubation of unit 20-A. Such microorganism colonies can be readily sampled for further analysis. Also shown on the rightside of unit 20-A are start-gate 28 and exit-gate 26. On the left side of unit 20-A is a bottle 60 containing beads 30.

The components used in multi-channel plating unit 20 and beads can be of any suitable rigid or semi-rigid material, such as plastic, wood, metal or any combination thereof. Preferably, plastic is used due to its ease of molding and ability to withstand sterilization, multiple washings, autoclaving and/or irradiation such as with ultraviolet light. Suitable plastics include polystyrene, polypropylene, polycarbonate or combinations thereof. Preferably the material is clear or nearly clear. Also preferred is that multi-channel plating unit 20 is reusable, so that used agar can be safely discarded or disposed of and the components of unit 20 can be reused over again.

Operation of the Multichannel Plating Unit.

Preferably, all items should be substantially sterile to prevent growth of extraneous microorganisms. Exit-gate 28 is secured to unit 24 and the microbial agar media is poured. After the media has solidified, exit-gate 26 is removed and start gate 28 is put in place. One or more beads are put into each lane above start-gate 28. A determined amount of liquid microbial aliquot containing, for example, a bacterial culture, is applied to beads 30 using a 12-channel pipette. The beads are more uniformly coated with the culture by agitating them against start-gate 28 or rolling them around the space between start-gate 28 and the end of unit 20. Start-gate 28 is then removed and beads 30 are rolled over the agar surface 100 just one time making a linear path down each respective lane, i.e. A, B, C, etc., eventually falling into the trap or exit alley 27. Unit 20-A can be tilted so that beads 30 can exit through aperture 25 for subsequent reuse or disposal. Unit 20-A is permitted to stand at room temperature for a time sufficient, usually an hour or less, to allow absorption of the liquid culture media by agar surface 100 (as applied to the agar surface by the rolling beads). Then, loose-fitting lid 40 is placed over unit 20-A, unit 20-A with lid 40 is inverted (i.e. turned over so that the agar surface 100 faces downward), and incubated under conditions suitable for the growth of the microorganisms being plated.

What is claimed is:

1. A method for plating microorganisms or cell culture, comprising:
   a) using an apparatus comprising:
      i) a tray having a bottom and sidewalls extending from said bottom;
      ii) a plurality of parallel dividers, each divider having a length and a height and being substantially uninterrupted along the entire length thereof;
      iii) means for maintaining said dividers substantially parallel within said tray, wherein said dividers are removable from said tray;
      iv) agar that fills said tray to a point less than the height of said dividers in said tray, wherein said agar has a surface for plating microorganisms or cell culture that is defined as a lane between two adjacent dividers or a lane between a divider and an adjacent sidewall; and
      v) beads that can fit between said substantially parallel dividers; and
   b) contacting said beads with a source of microorganisms or cell culture; and
   c) rolling said beads with said microorganisms or cell culture along said agar surface from one end of the tray to the opposite end to plate said microorganisms or cell culture.

2. The method according to claim 1 wherein said plurality of dividers comprises at least eleven dividers.

3. The method according to claim 1 comprising eleven dividers.

4. The method according to claim 1 wherein said tray and said dividers are plastic.

5. The method according to claim 1 wherein said tray and said dividers are selected from a plastic which is polycarbonate, polystyrene, polypropylene or combinations thereof.

6. The method according to claim 1 wherein said means for maintaining said dividers substantially parallel is at least one supporting rib.

7. The method according to claim 1 wherein said means for maintaining said dividers substantially parallel is at least two supporting ribs.

8. The method according to claim 1 wherein said means for maintaining said dividers substantially parallel is at least three supporting ribs.

9. The method according to claim 1 wherein said tray has an interior length and an interior width and said divider length is less that the length of the interior of said tray.

10. The method according to claim 9 wherein said divider length is about 75% to about 95% of the interior length of said tray.

11. The method according to claim 1 wherein said apparatus further comprises vi) a cover.

12. The method according to claim 11 wherein said cover is removable from said tray.

13. The method according to claim 1 wherein said beads are spherical.

14. The method according to claim 1 wherein said beads are glass.

15. The method according to claim 1 wherein said apparatus further comprises vii) a starting gate.

16. The method according to claim 1 wherein said dividers have at least one notch along the edge of the divider length.

17. The method according to claim 15 wherein said dividers have at least one notch along the edge of the divider length and said starting gate rests upon said notch in each of said dividers.

18. The method according to claim 1 wherein said apparatus further comprises viii) an exit-gate whose removal defines an exit-alley within said tray.

19. The method according to claim 18 wherein said exit-alley communicates with at least one sidewall of said tray having at least one aperture therein.

20. The method according to claim 1 wherein said tray and said dividers are substantially sterile.

21. An apparatus comprising:
   a) a tray having a bottom and sidewalls extending from said bottom;
   b) a plurality of parallel dividers, each divider having a length and a height and being substantially uninterrupted along the entire length thereof;
   c) means for maintaining said dividers substantially parallel within said tray, wherein said dividers are removable from said tray; and
   d) beads that can fit between said substantially parallel dividers from one end of the tray to the opposite end.

22. The apparatus according to claim 21 wherein said plurality of dividers comprises at least eleven dividers.

23. The apparatus according to claim 21 comprising eleven dividers.

24. The apparatus according to claim 21 wherein said tray and said dividers are plastic.

25. The apparatus according to claim 21 wherein said tray and said dividers are selected from a plastic which is polycarbonate, polystyrene, polypropylene or combinations thereof.

26. The apparatus according to claim 21 wherein said means for maintaining said dividers substantially parallel is at least one supporting rib.

27. The apparatus according to claim 21 wherein said means for maintaining said dividers substantially parallel is at least two supporting ribs.

28. The apparatus according to claim 21 wherein said means for maintaining said dividers substantially parallel is at least three supporting ribs.

29. The apparatus according to claim 21 wherein said tray has an interior length and an interior width and said divider length is less that the length of the interior of said tray.

30. The apparatus according to claim 29 wherein said divider length is about 75% to about 95% of the interior length of said tray.

31. The apparatus according to claim 21 further comprising a cover.

32. The apparatus according to claim 31 wherein said cover is removable from said tray.

33. The apparatus according to claim 21 wherein said beads are spherical.

34. The apparatus according to claim 21 wherein said beads are glass.

35. The apparatus according to claim 21 further comprising f) a starting gate.

36. The apparatus according to claim 21 wherein said dividers have at least one notch along the edge of the divider length.

37. The apparatus according to claim 35 wherein said dividers have at least one notch along the edge of the divider length and said starting gate rests upon said notch in each of said dividers.

38. The apparatus according to claim 21 further comprising g) an exit-gate whose removal defines an exit-alley within said tray.

39. The apparatus according to claim 38 wherein said exit-alley communicates with at least one sidewall of said tray having at least one aperture therein.

40. The apparatus according to claim 21 wherein said tray and said dividers are substantially sterile.

41. An apparatus comprising:
  a) a tray having a bottom and sidewalls extending from said bottom;
  b) a plurality of parallel dividers, each divider having a length and a height and being substantially uninterrupted along the entire length thereof;
  c) means for maintaining said dividers substantially parallel within said tray, wherein said dividers are removable from said tray;
  d) a cover for covering said tray and said dividers; and
  e) beads that can fit between said substantially parallel divider from one end of the tray to the opposite end.

42. The apparatus according to claim 41 further comprising f) a starting gate.

43. The apparatus according to claim 41 further comprising g) an exit-gate whose removal defines an exit-alley within said tray.

44. An apparatus comprising:
  a) a tray having a bottom and sidewalls extending from said bottom;
  b) a plurality of parallel dividers, each divider having a length and a height and being substantially uninterrupted along the entire length thereof;
  c) means for maintaining said dividers substantially parallel within said tray, wherein said dividers are removable from said tray;
  d) beads that fit between said substantially parallel dividers from one end of the tray to the opposite end; and
  e) agar that fills said tray to a point less than the height of said dividers in said tray, wherein said agar has a surface for plating microorganisms or cell culture that is defined as a lane between two adjacent dividers or a lane between a divider and an adjacent sidewall.

45. The apparatus according to claim 44 further comprising fe) a cover.

46. The apparatus according to claim 44 further comprising g) a starting gate.

47. The apparatus according to claim 44 further comprising h) an exit-gate whose removal defines an exit-alley within said tray.

48. An apparatus comprising:
  a) a tray having a bottom and sidewalls extending from said bottom;
  b) a plurality of parallel dividers, each divider having a length and a height and being substantially uninterrupted along the entire length thereof;
  c) means for maintaining said dividers substantially parallel within said tray, wherein said dividers are removable from said tray;
  d) a cover for covering said tray and said dividers;
  e) beads that can fit between said substantially parallel dividers from one end of the tray to the opposite end; and
  f) agar that fills said tray to a point less than the height of said dividers in said tray, wherein said agar has a surface for plating microorganisms or cell culture that is defined as a lane between two adjacent dividers or a lane between a divider and an adjacent sidewall.

49. The apparatus according to claim 48 further comprising g) a starting gate.

50. The apparatus according to claim 48 further comprising h) an exit-gate whose removal defines an exit-alley within said tray.

51. A kit comprising in a single package:
  a) a tray having a bottom and sidewalls extending from said bottom;
  b) a plurality of parallel dividers, each divider having a length and a height and being substantially uninterrupted along the entire length thereof;
  c) means for maintaining said dividers substantially parallel within said tray, wherein said dividers are removable from said tray; and
  d) beads that can fit between said substantially parallel dividers from one end of the tray to the opposite end.

52. The kit according to claim 51 further comprising e) a cover.

53. The kit according to claim 51 further comprising f) a starting gate.

54. The kit according to claim 51 further comprising g) an exit-gate whose removal defines an exit-alley within said tray.

* * * * *